United States Patent
Okada et al.

(10) Patent No.: US 7,678,959 B2
(45) Date of Patent: Mar. 16, 2010

(54) FILM BASE MATERIAL FOR ADHESIVE SKIN PATCH AND ADHESIVE SKIN PATCH

(75) Inventors: Katsuhiro Okada, Irabaki (JP); Seishi Suzuki, Ibaraki (JP); Yasuyuki Sasaki, Ibaraki (JP); Yuko Ueda, Ibaraki (JP); Toshiyuki Yoshikawa, Ibaraki (JP)

(73) Assignee: Nitto Denko Corporation, Osaka (JP)

(*) Notice: Subject to any disclaimer, the term of this patent is extended or adjusted under 35 U.S.C. 154(b) by 162 days.

(21) Appl. No.: 11/711,111

(22) Filed: Feb. 27, 2007

(65) Prior Publication Data

US 2008/0208099 A1 Aug. 28, 2008

(51) Int. Cl.
*A61F 15/00* (2006.01)

(52) U.S. Cl. .......................... 602/52; 602/54; 428/141; 424/448

(58) Field of Classification Search ................. 602/52
See application file for complete search history.

(56) References Cited

U.S. PATENT DOCUMENTS

| | | | | |
|---|---|---|---|---|
| 5,598,280 | A * | 1/1997 | Nishio et al. | 349/57 |
| 5,965,233 | A * | 10/1999 | Tojo et al. | 428/141 |
| 6,210,704 | B1 | 4/2001 | Sasaki et al. | |
| 6,319,588 | B1 * | 11/2001 | Ogawa et al. | 428/141 |
| 6,773,787 | B2 * | 8/2004 | Maas et al. | 428/141 |
| 2005/0031860 | A1 * | 2/2005 | Okada et al. | 428/354 |
| 2005/0031861 | A1 * | 2/2005 | Matsumura et al. | 428/354 |
| 2005/0169975 | A1 * | 8/2005 | Suzuki et al. | 424/448 |
| 2006/0257625 | A1 * | 11/2006 | Wakizaka | 428/141 |

FOREIGN PATENT DOCUMENTS

| | | | |
|---|---|---|---|
| JP | 53-2450 UM A | 1/1978 | |
| JP | 60-6775 A | 1/1985 | |
| JP | 7-39566 B | 5/1995 | |

(Continued)

OTHER PUBLICATIONS

Submission of Publications dated Oct. 20, 2008, Partial English Translation.
Submission of Publications with English translation.

*Primary Examiner*—Patricia Bianco
*Assistant Examiner*—Victoria Hicks
(74) *Attorney, Agent, or Firm*—Sughrue Mion, PLLC

(57) ABSTRACT

The present invention relates to a film base material for an adhesive skin patch, which includes an elastomer film unevenly having unevenness on at least one surface thereof, in which, in one unevenness in which the distance perpendicular to the surface of the elastomer film between the top of the unevenness and the bottom thereof is the longest among the plurality of unevenness, the distance is within the range of from 1 to 5 μm; in another unevenness in which the distance perpendicular to the surface of the elastomer film between the top of the unevenness and the bottom thereof is the shortest among the plurality of unevenness, the distance is within the range of from 0.1 to 0.9 μm; and the 10-point average roughness of the surface is within the range of from 0.5 μm to 3 μm, and which is decreased in glossy texture on the surface thereof and inconspicuous when it is applied to the skin or the like; and the adhesive skin patch including the film base material.

4 Claims, 2 Drawing Sheets

FOREIGN PATENT DOCUMENTS

| | | |
|---|---|---|
| JP | 2000-201965 A | 7/2000 |
| JP | 2000-201967 A | 7/2000 |
| JP | 2001-061953 A | 3/2001 |
| JP | 2003-190205 A | 8/2003 |
| JP | 2005-58341 A | 3/2005 |
| JP | 2006320358 | * 11/2006 |

* cited by examiner

FILM BASE MATERIAL FOR ADHESIVE SKIN PATCH AND ADHESIVE SKIN PATCH

FIELD OF THE INVENTION

The present invention relates to a film base material for an adhesive skin patch, and an adhesive skin patch. More specifically, the invention relates to a film base material for an adhesive skin patch and an adhesive skin patch, which are used, for example, for medical use or for sanitary materials.

BACKGROUND OF THE INVENTION

Pressure-sensitive adhesive tapes for medical use or for sanitary materials are required to prevent invasion of water, bacteria, viruses and the like from the outside and to have sufficient flexibility to follow up the curve or motion of the skin. For this reason, thin-layer elastomer films having a low elastic modulus similar to that of the skin have been generally used for film base materials as supports for such pressure-sensitive adhesive tapes. Further, the pressure-sensitive adhesive tapes for medical use or for sanitary materials such as dressing materials are demanded to be decreased in glossy texture to make them inconspicuous when they are applied to the skin.

In order to decrease glossy texture of the films to make them inconspicuous, for example, embossing or the like is performed on surface of the film to impart unevenness thereon.

However, the unevenness formed on the surface of the film by embossing is uniform, so that diffused reflection on the surface of the film increases to have a gloss in some cases, thereby becoming noticeable in some cases.

Patent Reference 1: JP-A-2003-190205

SUMMARY OF THE INVENTION

The invention has been made for solving the above-mentioned problem, and an object of the invention is to provide a film base material for an adhesive skin patch, which is decreased in glossy texture on the surface of the film base material and is inconspicuous when it is applied to the skin; and an adhesive skin patch including this film base material for an adhesive skin patch. Namely, the present invention relates to the following (1) to (5).

(1) A film base material for an adhesive skin patch, which comprises an elastomer film unevenly having a plurality of unevenness on at least one surface thereof, wherein, in one unevenness in which the distance perpendicular to the surface of the elastomer film between the top of the unevenness and the bottom thereof is the longest among the plurality of unevenness, the distance is within the range of from 1 to 5 µm;

in another unevenness in which the distance perpendicular to the surface of the elastomer film between the top of the unevenness and the bottom thereof is the shortest among the plurality of unevenness, the distance is within the range of from 0.1 to 0.9 µm; and the surface of the elastomer film has a 10-point average roughness within the range of from 0.5 µm to 3 µm.

(2) The film base material according to (1), wherein the elastomer film is formed by at least one material selected from the group consisting of a polyethylene, a polyvinyl chloride, an ethylene-vinyl acetate copolymer, a polyamide, a polyester, a polyurethane and an acrylic polymer.

(3) The film base material according to (2), wherein the polyurethane is an ether-based urethane resin.

(4) An adhesive skin patch, which comprises the film base material according to any one of (1) to (3) and a pressure-sensitive adhesive layer disposed on one side of the film base material.

(5) The adhesive skin patch according to (4), wherein the pressure-sensitive adhesive layer comprises a pressure-sensitive adhesive which is at least one member selected from the group consisting of an acrylic pressure-sensitive adhesive containing a (meth)acrylic acid ester as a main component, a silicone-based pressure-sensitive adhesive containing a polyorganosiloxane as a main component, and a urethane-based pressure-sensitive adhesive containing a polyether polyurethane and/or a polyester polyurethane as a main component.

DETAILED DESCRIPTION OF THE INVENTION

Figure 1:
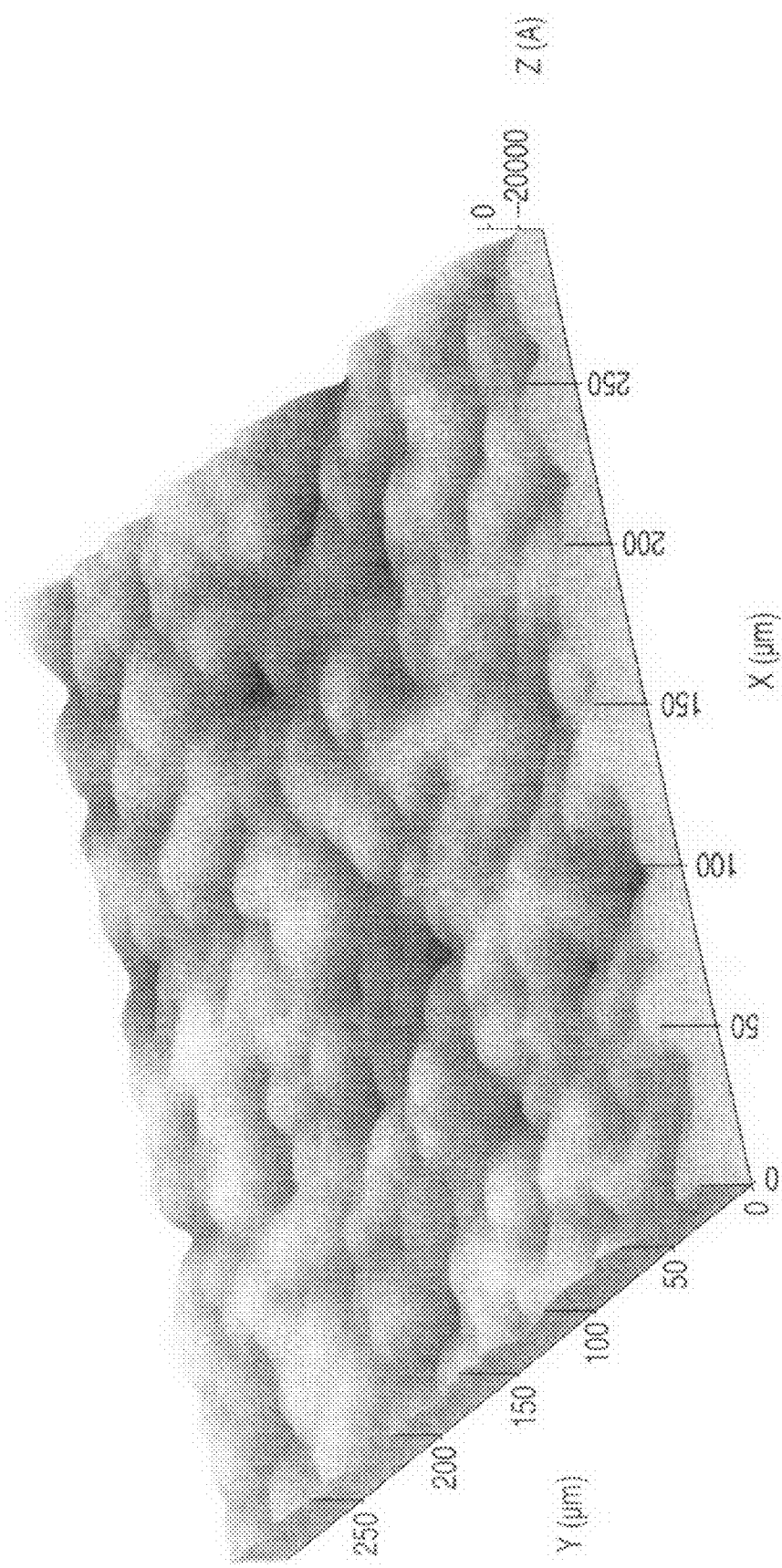
FIG. 1 is a view showing measurement results of a three-dimensional surface shape of a surface of a film base material for an adhesive skin patch of Example 1.

According to the film base material for an adhesive skin patch of the invention, an elastomer film unevenly has a plurality of unevenness on at least one surface thereof, in which, in one unevenness in which the distance perpendicular to the surface of the elastomer film between the top of the unevenness and the bottom thereof is the longest among the plurality of unevenness, the distance is within the range of from 1 to 5 µm; in another unevenness in which the distance perpendicular to the surface of the elastomer film between the top of the unevenness and the bottom thereof is the shortest among the plurality of unevenness, the distance is within the range of from 0.1 to 0.9 µm; and the 10-point average roughness of the surface is within the range of from 0.5 µm to 3 µm.

In the invention, a material for forming the above-mentioned elastomer film may be at least one selected from the group consisting of a polyethylene, a polyvinyl chloride, an ethylene-vinyl acetate copolymer, a polyamide, a polyester, a polyurethane and an acrylic polymer.

Further, the above-mentioned polyurethane may be an ether-based urethane resin.

According to the present invention, the adhesive skin patch includes a pressure-sensitive adhesive layer on one side of the above-mentioned film base material for an adhesive skin patch.

In this regard, the pressure-sensitive adhesive for forming the pressure-sensitive adhesive layer is preferably at least one member selected from the group consisting of an acrylic pressure-sensitive adhesive containing a (meth)acrylic acid ester as a main component, a silicone-based pressure-sensitive adhesive containing a polyorgano-siloxane as a main component, and a urethane-based pressure-sensitive adhesive containing a polyether polyurethane and/or a polyester polyurethane as a main component.

According to the invention, there can be provided a film base material for an adhesive skin patch, which is decreased in glossy texture on the surface thereof and inconspicuous when it is applied to the skin or the like; and the adhesive skin patch including the film base material.

The film base material for an adhesive skin patch of the invention includes an elastomer film which unevenly has a plurality of unevenness on at least one surface thereof. The elastomer film is preferably one having good followability to the skin and flexibility to be able to follow up the unevenness of the skin or the expansion and contraction thereof associated with bending or the like of the body. Examples of the material for forming such an elastomer film include a polyethylene, a polyvinyl chloride, an ethylene-vinyl acetate copolymer, a polyamide, a polyester, a polyurethane, an acrylic polymer and the like. In the invention, the elastomer film is preferably one that does not prevent perspiration from the skin. For example, a polyamide, a polyester, a polyurethane or an acrylic polymer is preferably used since a film formed by them is excellent in water vapor permeability. In particular, a polyesterpolyurethane, an ether-based urethane resin such as a polyetherpolyurethane, a polyetherpolyester or a polyetherpolyamide is preferably used.

When the elastomer film is formed by an ether-based urethane resin such as a polyetherpolyurethane, the ether-based urethane resin is obtainable by reacting a polyol component with a polyisocyanate component. As the polyol component as used herein, there is preferably used at least one member selected from the group consisting of polyoxytetramethylene glycol (hereinafter also abbreviated as "OTMG"), butanediol (hereinafter also abbreviated as "BD"), polyethylene glycol (hereinafter also abbreviated as "PEG"), and polypropylene glycol (hereinafter also abbreviated as "PPG"). Further, as the isocyanate component, there is preferably used, for example, diphenylmethane diisocyanate (hereinafter also abbreviated as "MDI").

The term "film" as used in the invention includes a sheet, and the term "sheet" conceptually includes a film.

As polyoxytetramethylene glycol, polyethylene glycol or polypropylene glycol used as the polyol component, there is preferably selected one having an appropriate molecular weight depending on its application. Preferred examples thereof include one having a weight-average molecular weight of 500 to 3,000.

In the invention, it is preferred that polyoxytetramethylene glycol, and polyethylene glycol and/or polypropylene glycol are used as the polyol component. In particular, it is preferred that the ether-based urethane resin contains 5 to 60% by weight of polyoxytetramethylene glycol and 10 to 50% by weight of polyethylene glycol, and it is more preferred that the ether-based urethane resin contains 5 to 45% by weight of polyoxytetramethylene glycol and 20 to 45% by weight of polyethylene glycol.

Further, use of, for example, a random copolymer of polyoxytetramethylene glycol and polyethylene glycol as the polyol component can ensure high moisture permeability while preventing water swellability, so that when water swellability is to be taken into consideration, it is desirable to use the random copolymer of polyoxytetramethylene glycol and polyethylene glycol.

In the invention, a chain extender can be additionally used. Although conventional chain extenders can be used as the chain extender, examples thereof include diols such as ethylene glycol, propylene glycol and butanediol, and diamines such as ethylenenediamine.

In the invention, additives generally used in films, such as an ultraviolet absorber, an antiaging agent, a filler, a pigment, a colorant, a flame retardant, and an antistatic can be added according to the necessity. The additives are used in usual amounts depending on their kind.

The ether-based urethane resin can be polymerized by using, for example, a one-shot method or a prepolymer method. Further, either bulk polymerization using no solvent or polymerization in a solution for decreasing viscosity may be performed.

The bulk polymerization will be described in detail below. Diol component is put in a reaction vessel, the temperature is adjusted to 50 to 80° C., and an isocyanate component is added with stirring to cause urethanation to occur. Further, a chain extender is added and reacted. Then, the reaction product is transferred to a tray, and kept at 100 to 150° C. for 4 hours or more to complete the reaction, thereby to obtain a bulky ether-based urethane resin.

Then, the bulky ether-based urethane resin is pulverized and formed into pellets. The resulting resin pellets are molten and then extruded into sheet form by using a T-die extruder or an inflation die extruder, thereby to form a film base material made of the ether-based urethane resin. The film base material extruded into sheet form is usually rolled up. Alternatively, the ether-based urethane resin is rolled and elongated to sheet form between two hot rolls by calendering, thereby forming a film base material made of the ether-based urethane resin, and the film base material is rolled up as needed. The film base material made of the ether-based urethane resin may also be formed by dissolving the resin pellets in a solvent such as N,N-dimethylamide, applying the resulting solution onto a release liner such as a polyester film by using a bar coater or the like, and drying it to remove the solvent.

In the invention, the thickness of the film base material made of the ether-based urethane resin or the like is preferably within the range of from 10 to 150 μm in the case of a pressure-sensitive adhesive sheet (adhesive skin patch) for medical use or for sanitary materials. When the thickness of the film is less than 10 μm, it tends to become difficult to handle the sheet when it is applied to or peeled from the skin, and the handleability thereof is decreased to a level at which its use is impracticable in ordinary usage. On the other hand, when the thickness of the film is more than 150 μm, moisture permeability is not sufficiently obtained, so that the sheet becomes unsuitable for an adhesive skin patch based on the assumption that it is applied to the skin. When the adhesive skin patch is used for dressing applications, it is particularly preferred that the thickness of the film is within the range of from 20 to 60 μm. Further, in applications where a thin adhesive skin patch is required, the thickness of the film is preferably within the range of from 10 to 50 μm. In the invention, the elastomer film unevenly has a plurality of unevenness on a surface thereof. The expression "unevenly has a plurality of unevenness" as used herein means that the height and size of the plurality of unevenness are not uniform, and that the positional relationship of the plurality of unevenness disposed is also not uniform. According to the invention, in one unevenness in which the distance perpendicular to the surface of the elastomer film between the top of the unevenness and the bottom thereof is the longest among the plurality of unevenness, the distance is within the range of from 1 to 5 μm, preferably from 1.5 to 4 μm, and more preferably from 2 to 3 μm. When it is more than 5 μm, the adhesive skin patch becomes conspicuous and appearance and touch thereof become impaired. When it is less than 1 μm, the plurality of unevenness becomes nearly uniform and the adhesive skin patch may become glossy. Additionally, in another unevenness in which the distance perpendicular to the surface of the elastomer film between the top of the unevenness and the bottom thereof is the shortest among the plurality of unevenness, the distance is within the range of from 0.1 to 0.9 μm, preferably from 0.15 to 0.8 μm, and more preferably from 0.2 to 0.7 μm. When it is more than 0.9 μm, the plurality of unevenness becomes nearly uniform and the adhesive skin patch may become glossy. When it is less than 0.1 μm, the unevenness is too small and the adhesive skin patch may become glossy. Further, the 10-point average roughness of the surface is within the range of from 0.5 µm to 3 µm. When it is more than 3 µm, the surface of the elastomer film becomes overly uneven and diffused reflection may occur. When it is less than 0.5 µm, the plurality of unevenness becomes nearly uniform and the adhesive skin patch may become glossy. The adhesive skin patch decreased in a gloss and inconspicuous when it is applied to the skin can be realized by designing so that the surface of the film unevenly has the plurality of unevenness.

In the invention, a plurality of unevenness can be unevenly formed on the surface of the film, for example, by placing the film extruded from an extruder on a mat-treated surface of another film subjected to mat treatment, and closely adhering the film thereto by applying pressure. In addition, it is preferred to appropriately design the shape of the mat-treated surface or appropriately adjust the pressure applied for close adhesion so that the distance perpendicular to the surface of the elastomer film between the top of the unevenness and the bottom thereof becomes within the specific range.

The adhesive skin patch of the invention has a pressure-sensitive adhesive layer on one side of the film base material for an adhesive skin patch. Preferably, it has a pressure-sensitive adhesive layer on one side of the film base material for an adhesive skin patch, which is made of the above-mentioned ether-based urethane resin. It is preferred that the pressure-sensitive adhesive layer is formed by at least one member selected from the group consisting of an acrylic pressure-sensitive adhesive containing a (meth)acrylic acid ester as a main component, a silicone-based pressure-sensitive adhesive containing a polyorganosiloxane as a main component, and a urethane-based pressure-sensitive adhesive containing a polyether polyurethane and/or a polyester polyurethane as a main component.

When the pressure-sensitive adhesive layer is formed by the acrylic pressure-sensitive adhesive, for example, with an acrylic acid ester-based polymer are mixed a carboxylic acid ester compatible with this acrylic acid ester-based polymer and a crosslinking agent according to the necessity, and the resulting mixture is subjected to crosslinking treatment, thereby being able to obtain the pressure-sensitive adhesive layer, provided that the carboxylic acid ester has 16 or more carbon atoms and is liquid or paste at room temperature.

The acrylic acid ester-based polymer is one mainly which contains a (meth)acrylic acid ester and is optionally copolymerized with a monomer copolymerizable therewith. Preferred examples of the (meth)acrylic acid esters include a (meth) acrylic acid alkyl ester in which the alkyl group has 2 or more carbon atoms, and preferably 2 to 18 carbon atoms. Examples thereof include an ethyl ester, a propyl ester, a butyl ester, a pentyl ester, a hexyl ester, an octyl ester, a nonyl ester, a decyl ester, a dodecyl ester and the like of (meth)acrylic acid. Among these (meth)acrylic acid esters, one or two or more thereof are preferably used. Further, these alkyl ester chains may be either linear or branched.

Examples of the monomers copolymerizable with the (meth)acrylic acid ester include carboxyl group-containing monomers such as (meth)acrylic acid, itaconic acid and maleic acid, hydroxyl group-containing monomers such as 2-hydroxyethyl (meth)acrylate and 2-hydroxypropyl (meth) acrylate, alkoxy group-containing monomers such as methoxyethyl (meth)acrylate, ethoxyethyl (meth)acrylate, butoxyethyl (meth)acrylate, methoxypolyethylene glycol (meth)acrylate and ethoxydiethylene glycol (meth)acrylate, styrene and styrene derivatives, vinyl monomers such as vinyl acetate and N-vinyl-2-pyrrolidone, and the like. One or two or more of these monomers can be used by copolymerizing with the (meth)acrylic acid ester.

It is desirable that the acrylic acid ester-based polymer has a glass transition temperature of 260° K or less. By adjusting the glass transition temperature of the acrylic acid ester-based polymer to 260° K or less, adhesion to the skin can be sufficiently exhibited, resulting in obtaining a pressure-sensitive adhesive layer desirable as the one for a pressure-sensitive adhesive sheet for medical use or for sanitary materials.

The acrylic acid ester-based polymer can be obtained by a conventional polymerization method such as a solution polymerization method, an emulsion polymerization method or a suspension polymerization method. Further, it can be obtained by radical polymerization by using a radical polymerization initiator such as a peroxide-based compound or an azo-based compound.

The carboxylic acid ester compatible with the acrylic acid ester-based polymer is preferably liquid or paste at room temperature. When a carboxylic acid ester in solid form such as waxy form is mixed to form a pressure-sensitive adhesive layer, adhesion is decreased in some cases.

In the invention, a gel pressure-sensitive adhesive layer can be obtained by mixing the acrylic acid ester-based polymer, the carboxylic acid ester and the crosslinking agent to form at least partially a crosslinked body. The pressure-sensitive adhesive layer thus obtained can decrease the elastic modulus in minute deformed regions, which causes adhesion (wettability) of the surface of the pressure-sensitive adhesive layer to the unevenness of the surface of the skin to be improved, thereby being able to exhibit good adhesion to the skin. Moreover, when the adhesive skin patch is peeled, stress applied to the surface of the skin can be released or dispersed. Accordingly, it has advantages of scarcely giving physical irritation onto the surface of the skin when the adhesive skin patch is peeled off, scarcely causing the stratum corneum of the surface of the skin to be peeled off, and extremely decreasing damages of the skin.

As the carboxylic acid esters preferably used in the invention, there are used esters of phthalic acid, maleic acid, adipic acid, stearic acid and various fatty acids with alkyl alcohols, esters of such acids with polyhydric alcohols such as ethylene glycol and glycerol, and the like. Examples thereof include esters using monohydric alcohols, such as ethyl myristate, isopropyl myristate, isopropyl palmitate, butyl stearate, isopropyl isostearate, hexyl laurate, cetyl lactate, myristyl lactate, diethyl phthalate, dioctyl phthalate, octyldodecyl myristate, octyldodecyl oleate, hexyldecyl dimethyloctanoate, cetyl 2-ethylhexanoate, isocetyl 2-ethylhexanoate, stearyl 2-ethylhexanoate and dioctyl succinate, and esters using dihydric or higher polyhydric alcohols, such as propylene glycol dicaprylate, propylene glycol dicaprate, propylene glycol diisostearate, glyceryl monocaprylate, glyceryl tricaprylate, glyceryl tri-2-ethylhexannoate, glyceryl tricaprinate, glyceryl trilaurate, glyceryl triisostearate, glyceryl trioleate and trimethylolpropane tri-2-ehtylhexanoate.

In the invention, when the above-mentioned carboxylic acid esters are blended, at least one kind thereof is dissolved in the acrylic acid ester-based polymer. Although the blending amount of the carboxylic acid is not particularly limited, the carboxylic acid ester is for example added in an amount within the range of from 30 to 100 parts by weight based on 100 parts by weight of the acrylic acid ester-based polymer.

In the invention, when the acrylic acid ester-based polymer in which the above-mentioned carboxylic acid ester is dissolved is used, it is necessary that a crosslinked body is partially formed. In order to form the crosslinked body, crosslinking treatment is performed. For example, chemical crosslinking treatment may be performed by using an organic peroxide compound, an isocyanate compound, an organic metal salt, a metal chelate, an epoxy compound or the like, or physical crosslinking treatment may be performed by using ionizing radiation.

Further, a drug can be optionally added to the resin composition (pressure-sensitive adhesive) for forming the pressure-sensitive adhesive layer, thereby forming the adhesive skin patch.

The drug as used herein is not particularly limited, and a drug that can be administered to a mammal such as a human through the skin thereof, namely a percutaneously absorbable drug, is preferred. Specifically, such drugs include, for example, a systemic anesthetic, a hypnotic-sedative drug, an antiepileptic, an analgesic antipyretic antiphlogistic, an antivertiginous drug, a psychoneurotic drug, a local anesthetic, a skeletal muscle relaxant, an autonomic drug, a spasmolytic, an antiparkinson drug, an antihistamic drug, a cardiac stimulant, an antiarrhythmic drug, a diuretic, an antihypertensive drug, a vasoconstrictor, a coronary vasodilator, a peripheral vasodilator, a drug for arteriosclerosis, a circulatory drug, a respiratory stimulant, an antitussive expectorant drug, a hormone drug, an external drug for purulent disease, an analgesic-antipruritic-astringent-antiphlogistic drug, a drug for parasitic dermatosis, a hemostatic drug, a gout suppressant, an antidiabetic drug, an anticancer drug, an antibiotic, a chemotherapeutic drug, a narcotic drug, an antismoking aid and the like.

The content of the drug is not particularly limited so long as it is within such a range that the effect of the percutaneously absorbable drug is satisfied and that the adhesion characteristics of the pressure-sensitive adhesive are not impaired. However, the drug is contained preferably in an amount of from 0.1 to 60% by weight and more preferably in an amount of from 0.5 to 40% by weight. When it is Less than 0.1% by weight, it results in the possibility of an insufficient therapeutic effect. On the other hand, when it exceeds 60% by weight, it results in the possibility of the occurrence of skin irritation and the possibility of economical disadvantage.

In the resin composition (pressure-sensitive adhesive) for forming the pressure-sensitive adhesive layer, there may be blended various additives including plasticizers such as glycerol and polyethylene glycol, water-soluble or water-absorbing resins such as polyacrylic acid and polyvinylpyrrolidone, tackifiers such as rosin-based, terpene-based and petroleum-based tackifiers, various types of softening agents, fillers and pigments. In particular, when a carboxylic acid ester having an unsaturated bond is used as the carboxylic acid ester, it is feared that the physical properties will change due to oxidation deterioration caused by oxygen in the atmosphere, thus failing to exhibit desired characteristics. Accordingly, it is preferred that a conventional antioxidant is blended in the resin composition (pressure-sensitive adhesive) in such a case.

The thickness of the pressure-sensitive adhesive layer is preferably set in the range of from 10 to 100 µm. When the thickness of the pressure-sensitive adhesive layer is less than 10 µm, sufficient adhesion is not exhibited during application to the skin in some cases. On the other hand, when the thickness of the pressure-sensitive adhesive layer exceeds 100 µm, permeability of water vapor on a level required for an adhesive skin patch cannot be obtained in some cases.

According to the invention, by using the adhesive skin patch, there can be formed a medical tape or sheet such as an adhesive plaster. For example, the adhesive skin patch can be cut in an appropriate size to form an adhesive plaster, or a coating material for coating a wounded portion, a protector used after a surgical operation, a medical tape or sheet such as a cover material for a needle insertion portion of a catheter or gauze, Further, the adhesive skin patch can be combined with another base material or the like to form a medical product such as a tape for fixing or a tape for holding an instrument. In this regard, it goes without saying that the base material for an adhesive skin patch and the adhesive skin patch of the invention can also be used for applications other than the above-mentioned medical applications so long as they are applied to the skin. For example, they can be used for an adhesive pressure-sensitive pierce, a tape for tattoo, a tape for fixing a wig, a tape for artificial hair implant and the like.

EXAMPLES

The present invention will be illustrated in greater detail with reference to the following examples, but the invention should not be construed as being limited thereto. Further, measuring methods and evaluation methods used in the following examples are indicated below.

(Measuring Methods and Evaluation Methods)

(1) Measurement of Surface Shape of Surface of Film Base Material for Adhesive Skin Patch A film base material for an adhesive skin patch was cut out in a size of 10 mm×10 mm, and fixed onto a glass plate with a double-faced adhesive tape. The surface shape thereof was measured using a contact finger type surface shape measuring instrument (Tencor P-11, manufactured by KLA-Tencor Corporation) under conditions of a measuring length of 300 µm, a scanning speed of 100 µm/sec, a scanning number of 150 times and a load of 3 mg to determine the 10-point average roughness of the surface. Further, the longest distance perpendicular to the surface of the elastomer film between the top of the unevenness and the bottom thereof in one unevenness among the plurality of unevenness and the shortest distance perpendicular to the surface of the elastomer film between the top of the unevenness and the bottom thereof in another unevenness among the plurality of unevenness were determined.

(2) Evaluation of Surface Gloss in Application

An adhesive skin patch was applied to the skin and visually observed to evaluate whether it has glossy texture or not, and whether it is conspicuous or not.

Example 1

In a reaction vessel equipped with a condenser, a heater, a thermometer and a stirrer, 38 g of polyoxytet:ramethylene glycol (OTMG) having a weight-average molecular weight of 1,000, 26 g of polyethylene glycol (PEG) having a weight-average molecular weight of 2,000 and 6 g of 1,4-butanediol (BD) were placed as polyols and mixed. The temperature of the resulting mixture was adjusted to 70° C., and, as a polyisocyanate, 30 g of methylene diphenyldiisocyanate (MDI) adjusted to 50° C. was added thereto with stirring, followed by stirring for 5 minutes. Thereafter, the reaction product was transferred to a tray, which was placed in a hot-air dryer and aged at 140° C. for 5 hours to obtain a bulky ether-based urethane resin. The resulting bulky ether-based urethane resin was placed in a double-screw type kneader and melted by heating. Then, the melted resin was extruded by using a T-die type extruder in order to have a thickness of 30 µm. The resulting film was placed on a mat-treated surface of a drawn polypropylene film subjected to mat treatment, and closely adhered thereto by using a rubber roll, thereby preparing a film base material for an adhesive skin patch, which has a plurality of unevenness on its surface.

Figure 2:
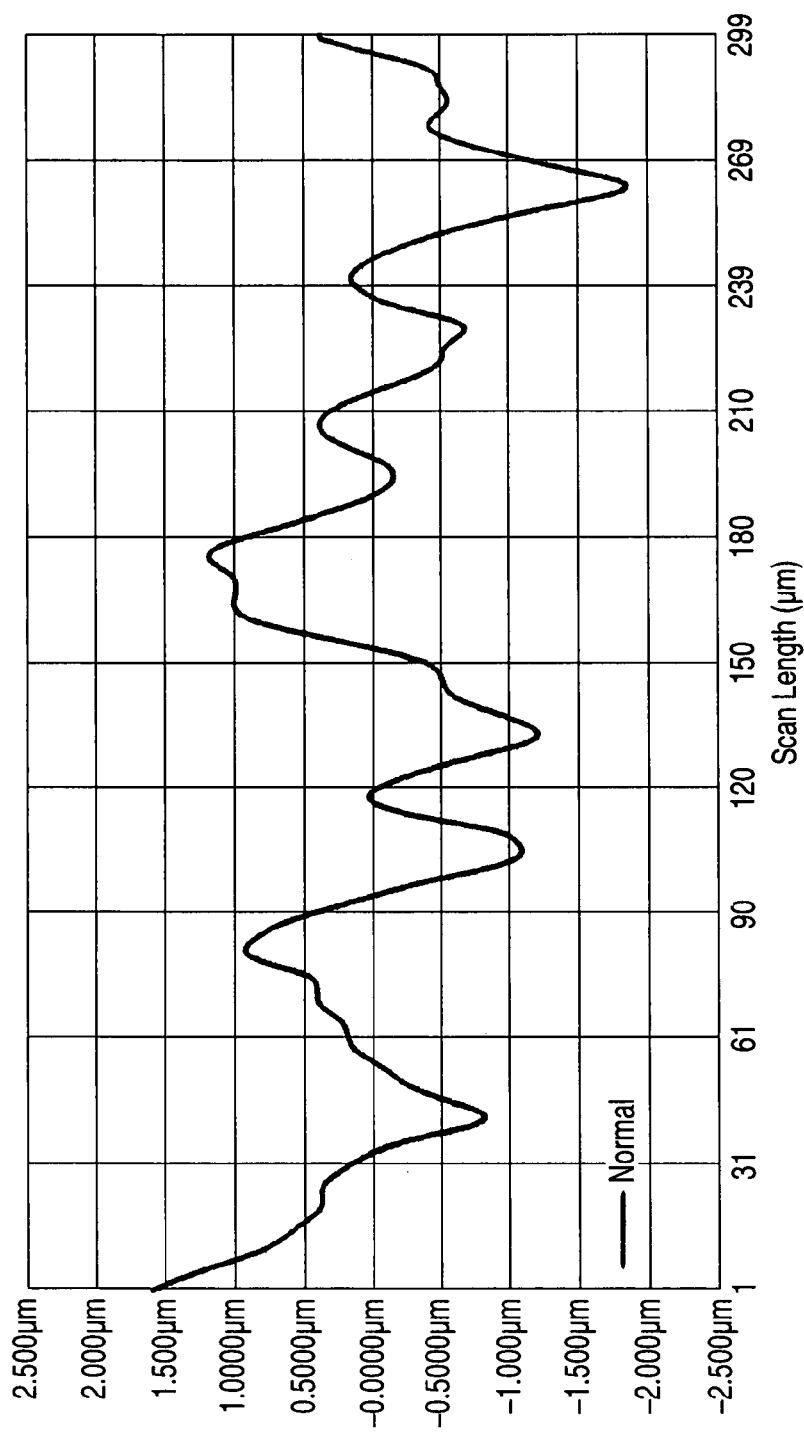
FIG. 2 is a view showing a two-dimensional profile of a surface of a film base material for an adhesive skin patch of Example 1.

For the resulting film base material for an adhesive skin patch, the surface shape was measured to determine the 10-point average roughness and each of the distance perpendicular to the surface of the elastomer film between the top of the unevenness and the bottom thereof in the plurality of unevenness. The results obtained by the measurement of the surface shape are shown in FIG. 1 and FIG. 2. FIG. 1 is a view showing measurement results of a three-dimensional surface shape of the surface, and FIG. 2 is a view showing a two-dimensional profile of the surface.

Then, a pressure-sensitive adhesive layer was formed on the resulting film base material for an adhesive skin patch.

Isononyl acrylate (NA), methoxyethyl acrylate (MEA) and acrylic acid (AA) were copolymerized to obtain an acrylic acid alkyl ester-based polymer, provided that the compounding ratio in the acrylic acid alkyl ester-based polymer was NA:MEA:AA=65:30:5 in weight ratio. In toluene, 100 parts by weight (solid content) of the resulting acrylic acid alkyl ester-based polymer, 60 parts by weight of glyceryl tricaprylate (GTC) as a carboxylic acid ester component, and 0.2 part by weight of a trifunctional isocyanate compound as a crosslinking agent component were mixed to prepare a solution for a pressure-sensitive adhesive layer (concentration: 33%). This solution for a pressure-sensitive adhesive layer was applied onto a release-treated surface of a paper separator subjected release treatment in order to have a thickness after drying of 30 μm, and dried at 110° C. for 3 minutes in a hot-air dryer to form a pressure-sensitive adhesive layer.

The film base material made of the ether-based urethane resin prepared was applied onto the resulting pressure-sensitive adhesive layer, and then stored in an atmosphere of 60° C. for 3 days in a hot-air dryer to perform aging, thereby completing crosslinking reaction of the pressure-sensitive adhesive layer to prepare an adhesive skin patch for a dressing material. The resulting adhesive skin patch was applied to the skin, and the evaluation of a surface gloss was performed. As a result, it was revealed that a surface of the adhesive skin patch generated no diffused reflection, had decreased glossy texture, and was inconspicuous when it was applied.

As apparent from FIG. 1, it was revealed that the film base material for an adhesive skin patch of Example 1 unevenly had a plurality of unevenness on the surface thereof. Further, FIG. 2 showed that the longest distance perpendicular to the surface of the elastomer film between the top of the unevenness and the bottom thereof in one unevenness of the film base material for an adhesive skin patch of Example 1 was 2.3 μm, while the shortest distance perpendicular to the surface of the elastomer film between the top of the unevenness and the bottom thereof in another unevenness was 0.3 μm. Still further, it was revealed that the 10-point average roughness of the film base material for an adhesive skin patch of Example 1 was 1.8 μm. That is to say, it is revealed that the diffused reflection on the surface can be decreased by unevenly having the plurality of unevenness in which, in one unevenness in which the distance perpendicular to the surface of the elastomer film between the top of the unevenness and the bottom thereof is the longest among the plurality of unevenness, the distance is within the range of from 1 to 5 μm; in another unevenness in which the distance perpendicular to the surface of the elastomer film between the top of the unevenness and the bottom thereof is the shortest among the plurality of unevenness, the distance is within the range of from 0.1 to 0.9 μm; and the 10-point average roughness is from 0.5 μm to 3 μm, thereby being able to decrease the surface gloss, which made it possible to realize the adhesive skin patch inconspicuous when it is applied.

In addition, this adhesive skin patch had moderate adhesive force, and was excellent in followability to the skin or the like.

The adhesive skin patch of the invention can be used in sheet form, tape form or the like having various sizes, and further can also be stored in roll form. These adhesive skin patches can be used in adhesive skin applications, for example, in the medical and sanitary fields and the fields of external applications and the like. Specifically, they are suitably used in adhesive plasters, adhesive bandages, dressing materials and the like.

While the present invention has been described in detail and with reference to specific embodiments thereof, it will be apparent to one skilled in the art that various changes and modifications can be made therein without departing from the scope thereof.

This application is based on Japanese patent application No. 2005-143520 filed May 17, 2005, the entire contents thereof being hereby incorporated by reference.

Further, all the documents described herein are incorporated by reference.

What is claimed is:

1. An adhesive skin patch, which comprises a film base material and a pressure-sensitive adhesive layer disposed on one side of the film base material,
   wherein the film base comprises an elastomer film unevenly having a plurality of unevenness on at least one surface thereof, wherein, in one unevenness in which the distance perpendicular to the surface of the elastomer film between the top of the unevenness and the bottom thereof is the longest among the plurality of unevenness, the distance is within the range of from 1 to 5 μm;
   in another unevenness in which the distance perpendicular to the surface of the elastomer film between the top of the unevenness and the bottom thereof is the shortest among the plurality of unevenness, the distance is within the range of from 0.1 to 0.9 μm; and
   the surface of the elastomer film has a 10-point average roughness within the range of from 0.5 μm to 3 μm.

2. The adhesive skin patch according to claim 1, wherein the elastomer film is formed by at least one material selected from the group consisting of a polyethylene, a polyvinyl chloride, an ethylene-vinyl acetate copolymer, a polyamide, a polyester, a polyurethane and an acrylic polymer.

3. The adhesive skin patch according to claim 2, wherein the polyurethane is an ether-based urethane resin.

4. The adhesive skin patch according to claim 1, wherein the pressure-sensitive adhesive layer comprises a pressure-sensitive adhesive which is at least one member selected from the group consisting of an acrylic pressure-sensitive adhesive containing a (meth)acrylic acid ester as a main component, a silicone-based pressure-sensitive adhesive containing a polyorganosiloxane as a main component, and a urethane-based pressure-sensitive adhesive containing a polyether polyurethane and/or a polyester polyurethane as a main component.

* * * * *